US011253227B2

(12) United States Patent
Bai

(10) Patent No.: US 11,253,227 B2
(45) Date of Patent: Feb. 22, 2022

(54) PROBE ROBOT DEVICE

(71) Applicant: VINNO TECHNOLOGY (SUZHOU) CO., LTD., Suzhou (CN)

(72) Inventor: Yinzhang Bai, Suzhou (CN)

(73) Assignee: VINNO TECHNOLOGY (SUZHOU) CO., LTD., Jiangsu (CN)

( * ) Notice: Subject to any disclaimer, the term of this patent is extended or adjusted under 35 U.S.C. 154(b) by 501 days.

(21) Appl. No.: 16/325,578

(22) PCT Filed: Feb. 16, 2017

(86) PCT No.: PCT/CN2017/073775
§ 371 (c)(1),
(2) Date: Feb. 14, 2019

(87) PCT Pub. No.: WO2018/036110
PCT Pub. Date: Mar. 1, 2018

(65) Prior Publication Data
US 2019/0175143 A1 Jun. 13, 2019

(30) Foreign Application Priority Data

Aug. 26, 2016 (CN) .......................... 201610729137.X

(51) Int. Cl.
*A61B 8/00* (2006.01)
*A61B 34/30* (2016.01)
*A61B 17/00* (2006.01)

(52) U.S. Cl.
CPC ............ *A61B 8/4254* (2013.01); *A61B 8/429* (2013.01); *A61B 8/4461* (2013.01); *A61B 34/30* (2016.02);
(Continued)

(58) Field of Classification Search
CPC .. A61B 2017/00106; A61B 2090/3612; A61B 2090/378; A61B 34/30;
(Continued)

(56) References Cited

U.S. PATENT DOCUMENTS 4,099,420 A * 7/1978 Stouffer ................. A22B 5/007
73/629
2005/0154295 A1 7/2005 Quistgaard et al.
(Continued)

FOREIGN PATENT DOCUMENTS

CN 101229069 A 7/2008
CN 201256981 Y 6/2009
(Continued)

OTHER PUBLICATIONS

International Search Report for PCT/CN2017/073775 dated May 25, 2017 and its English translation provided by WIPO.
(Continued)

*Primary Examiner* — Mark D Remaly
(74) *Attorney, Agent, or Firm* — Ladas & Parry, LLP

(57) ABSTRACT

The present invention discloses a probe robot device, comprising: a probe housing; a probe transducer connected to the probe housing and configured to collect a lesion; and a probe connecting line connected to the probe transducer and configured to transmit the lesion information collected by the probe transducer; wherein the probe robot device further comprises a probe movement mechanism, and the probe movement mechanism is capable of controlling the probe transducer to respectively perform rotational movement around at least two angled axes within a preset angle range. According to the probe robot device in the present invention, the probe transducer can perform the rotation and positioning movements in multiple directions, so that the informa- (Continued)

tion of the scanned and examined lesion is more comprehensive, and the operation is simpler and more convenient.

11 Claims, 10 Drawing Sheets

(52) U.S. Cl.
CPC ... *A61B 8/4209* (2013.01); *A61B 2017/00106* (2013.01)

(58) Field of Classification Search
CPC ..... A61B 8/4209; A61B 8/4254; A61B 8/429; A61B 8/4461
See application file for complete search history.

(56) References Cited

U.S. PATENT DOCUMENTS

2012/0271173 A1 10/2012 Li
2014/0121520 A1* 5/2014 Wang .................. A61B 8/0825
600/444

FOREIGN PATENT DOCUMENTS

| | | |
|---|---|---|
| CN | 202397505 U | 8/2012 |
| CN | 102743188 A | 10/2012 |
| CN | 102988081 A | 3/2013 |
| CN | 103750864 A | 4/2014 |
| CN | 104825189 A | 8/2015 |
| CN | 104856720 A | 8/2015 |
| CN | 205041433 U | 2/2016 |
| CN | 205094484 U | 3/2016 |
| CN | 105662461 A | 6/2016 |
| CN | 106344066 A | 1/2017 |
| EP | 1103222 B1 | 5/2001 |

OTHER PUBLICATIONS

Written Opinion for PCT/CN2017/073775 dated May 25, 2017 and its English translation provided by Google Translate.
First Office action dated Nov. 1, 2018 for related Chinese Application 201610729137.X provided by Global Dossier and translation provided by Google translate.

* cited by examiner

PROBE ROBOT DEVICE

CROSS-REFERENCE TO RELATED APPLICATIONS

The present application is a U.S. national phase application of PCT Application No. PCT/CN2017/073775 filed on Feb. 16, 2017, which claims the priority to the Chinese Patent Application No. 201610729137.X titled "Probe Robot Device" filed on Aug. 26, 2016, both of which are incorporated herein by reference in their entireties.

TECHNICAL FIELD

The present invention relates to a probe robot device, and in particular to an ultrasonic probe robot device, which is applied to ultrasonic detection apparatus for scanning bodies of people or animals and collecting data.

BACKGROUND

Ultrasonic diagnostic equipment uses the ultrasonic detection technology to understand the data and morphology of human body tissues and structures by ultrasonic measurement. At present, the ultrasonic diagnostic equipment used in the art generally comprises a body and a probe. The probe is inserted on the body, and ultrasonic waves are emitted by a transducer of the probe. The target to be measured is scanned and detected, and the obtained scan data are fed back to the body for further processed.

In the prior art, at present, the functions of the probes are relatively single, only having the function of collecting a lesion. When performing an ultrasonic examination, the doctor needs to hold the probe to scan the body part of a patient, and the examination of each patient is performed completely depending on the experience of the doctor. The operation of the doctor is tedious and the work is hard. When there are many persons to be examined, the arms of the doctor will be very tired. Moreover, experienced doctors are required, and the requirements on the doctors are high. The patients can only be examined in hospital. Every time the patient queues for examination in hospital, there is great waste in time and money. These are all because that the relatively high level of expertise of the people who operate the probe for scanning and examination is required, and the fully automatic probes cannot be realized.

SUMMARY

An objective of the present invention is to provide a probe robot device. The operation of the probe robot device is simpler and more convenient, and a probe transducer can more comprehensively scan and examine lesion information.

In order to achieve the above objective, the present invention provides a probe robot device, comprising: a probe housing; a probe transducer connected to the probe housing, the probe transducer being configured to collect a lesion; and a probe connecting line connected to the probe transducer, the probe connecting line being configured to transmit the lesion information collected by the probe transducer, wherein the probe robot device further comprises a probe movement mechanism, and the probe movement mechanism is capable of controlling the probe transducer to respectively perform rotational movement around at least two angled axes within a preset angle range.

As an improvement of one embodiment of the present invention, the probe movement mechanism comprises a probe rotating structure, and the probe rotating structure is capable of controlling the probe transducer to rotate around a vertical axis perpendicular to the surface of the lesion.

As a further improvement of one embodiment of the present invention, the probe movement mechanism comprises a probe swinging structure, the probe swinging structure is capable of controlling the probe transducer to perform rotational movement around an axis parallel to a plane of the lesion within a range less than 180 degrees, the probe swinging structure is connected to the probe rotating structure, and the probe rotating structure is capable of controlling the probe swinging structure and the probe transducer to rotate together around a vertical axis perpendicular to the surface of the lesion.

As a further improvement of one embodiment of the present invention, the probe rotating structure comprises a steering engine and a steering engine connecting arm connected between the steering engine and the probe transducer, and the steering engine controls the rotational movement of the probe transducer by the steering engine connecting arm.

As a further improvement of one embodiment of the present invention, the probe movement mechanism comprises a probe swinging structure, and the probe swinging structure is capable of controlling the probe transducer to perform rotational movement around an axis parallel to a plane of the lesion within a range less than 180 degrees.

As a further improvement of one embodiment of the present invention, the probe swinging structure comprises a probe front and back swinging structure for controlling swinging type rotational movement of the probe transducer in front and back directions, and/or a probe left and right swinging structure for controlling swinging type rotational movement of the probe transducer in left and right directions.

As a further improvement of one embodiment of the present invention, the probe robot device further comprises a bracket for mounting the probe left and right swinging structure, the bracket is connected to the probe front and back swinging structure, and the probe front and back swinging structure is capable of driving the bracket and the probe left and right swinging structure to perform front and back swinging type rotational movement together.

As a further improvement of one embodiment of the present invention, the probe swinging structure comprises a steering engine and a steering engine connecting arm connected between the steering engine and the probe transducer, and the steering engine controls the rotational movement of the probe transducer by the steering engine connecting arm.

As a further improvement of one embodiment of the present invention, the probe robot device further comprises a probe pressure detecting structure, and the probe pressure detecting structure is configured to detect a pressure of the probe against a detected surface.

As a further improvement of one embodiment of the present invention, the probe robot device further comprises an up and down movement mechanism for controlling the probe transducer to move in a direction close to or away from the detected surface, and when the pressure is outside the preset range, the up and down movement mechanism will control the movement of the probe transducer according to a signal given by the pressure detecting structure, such that the pressure is within the preset range.

As a further improvement of one embodiment of the present invention, the probe robot device further comprises a prompting module, and when the pressure reaches a preset value, the prompting module will perform corresponding prompting.

As a further improvement of one embodiment of the present invention, the probe robotic device further comprises a robotic arm, and the robotic arm is capable of controlling the probe transducer to move in a direction close to or away from the detected surface and/or move on the detected surface.

As a further improvement of one embodiment of the present invention, the probe housing is detachably connected to the probe movement mechanism, and the probe movement mechanism drives the probe transducer to perform rotational movement by driving the probe housing.

Compared with the prior art, the present invention has the beneficial effects that the probe transducer of the probe robot device according to the present invention can perform the rotation movements of multiple directions and positioning, so that the lesion information obtained by scanning and examining can be more comprehensive, and the operation is simpler and more convenient. Moreover, the probe robot device according to the present invention has lower requirements on a doctor and can greatly reduce the workload of the doctor. In addition, the probe sales group of the probe robot device according to the present invention is no longer a medical institution, and can enter thousands of households. Thus, the probe robot device can be used by everyone.

DETAILED DESCRIPTION

Figure 1:
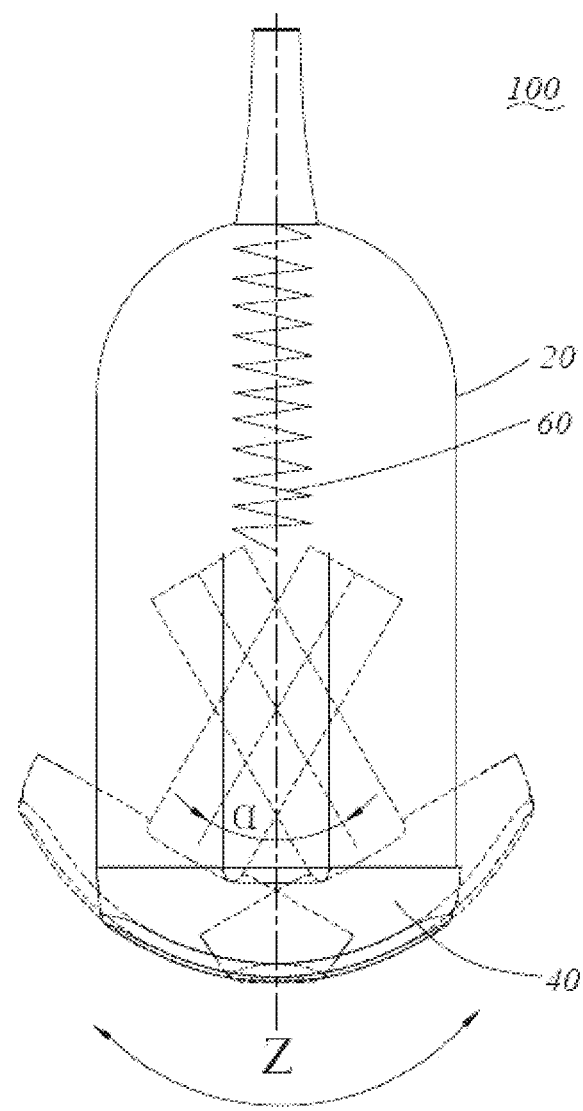
FIG. 1 is a front view of a probe in a probe robot device according to a preferred embodiment of the present invention, showing the degree of freedom of the probe in a first direction of the space.

The present invention will be described in detail below in conjunction with the specific embodiments shown in the drawings. However, the embodiments are not intended to limit the present invention, and the changes on the structures, methods, or functions made by those ordinary skilled in the art in accordance with the embodiments are included in the scope of the present invention.

Figure 2:
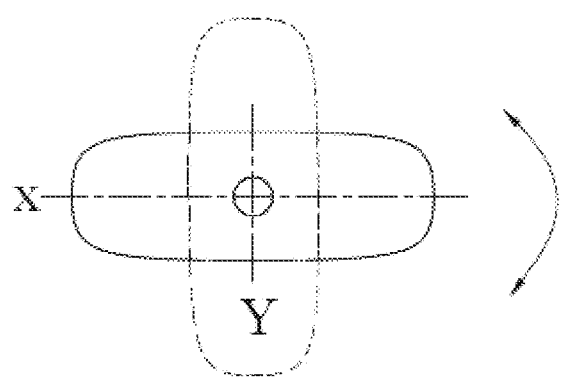
FIG. 2 is a top view of the probe of FIG. 1, showing the degree of freedom of the probe in a second direction of the space.
Figure 3:
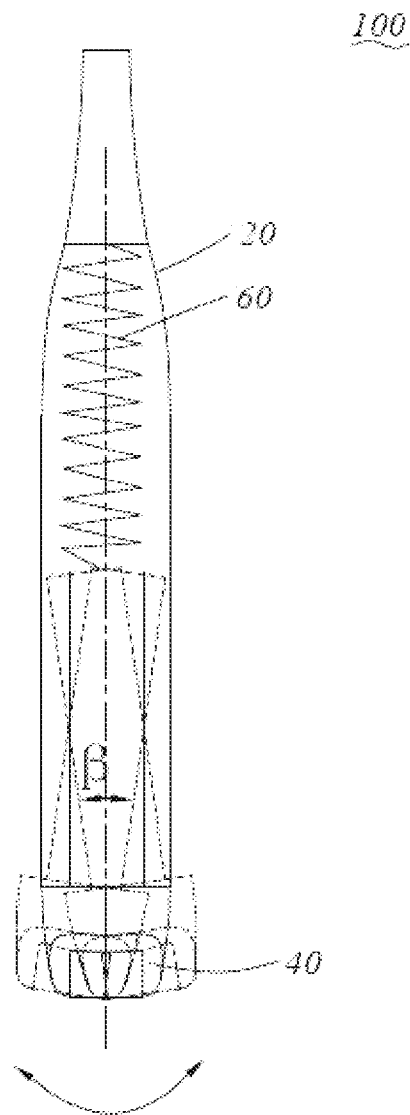
FIG. 3 is a left side view of the probe of FIG. 1, showing the degree of freedom of the probe in a third direction of the space.
Figure 4:
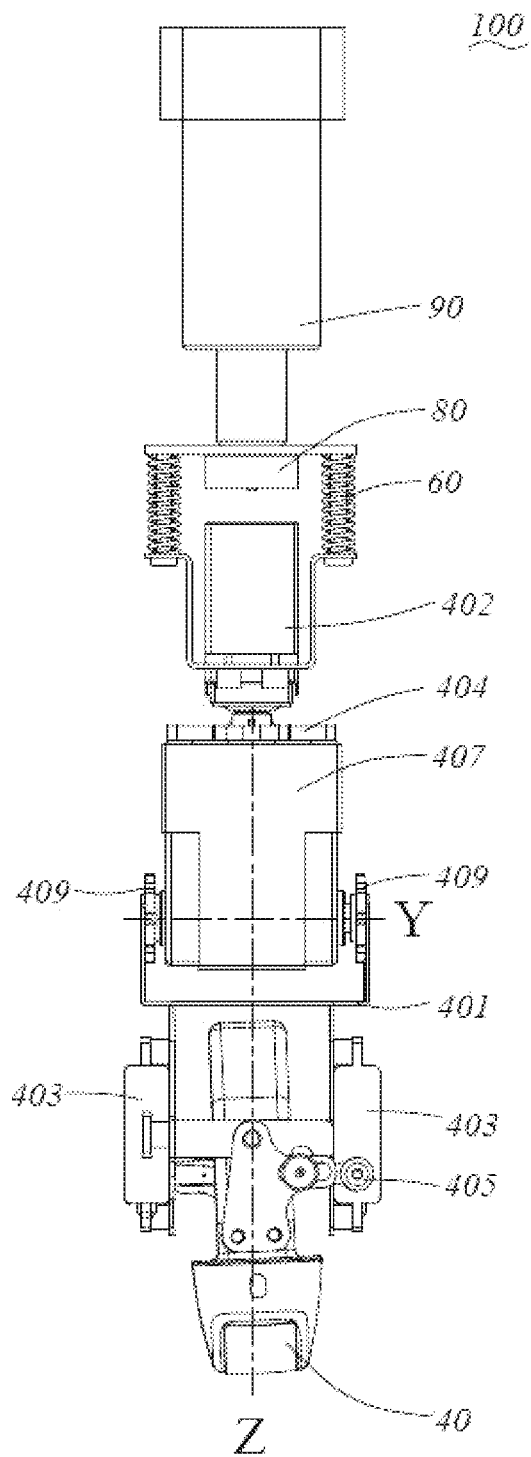
FIG. 4 is a schematic diagram of the composition principle of a specific mechanism of the probe robot device according to a preferred embodiment of the present invention.
Figure 5:
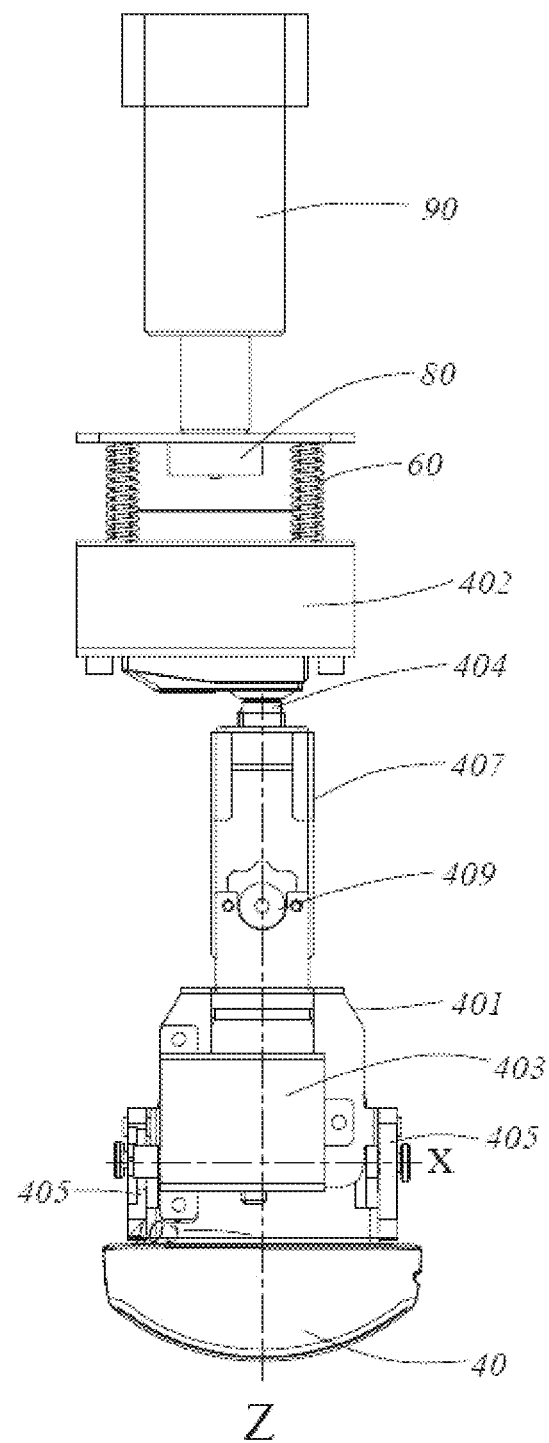
FIG. 5 is a schematic view of the probe of the probe robot device of FIG. 4 rotating around a first axis, wherein the probe is in a first position.
Figure 6:
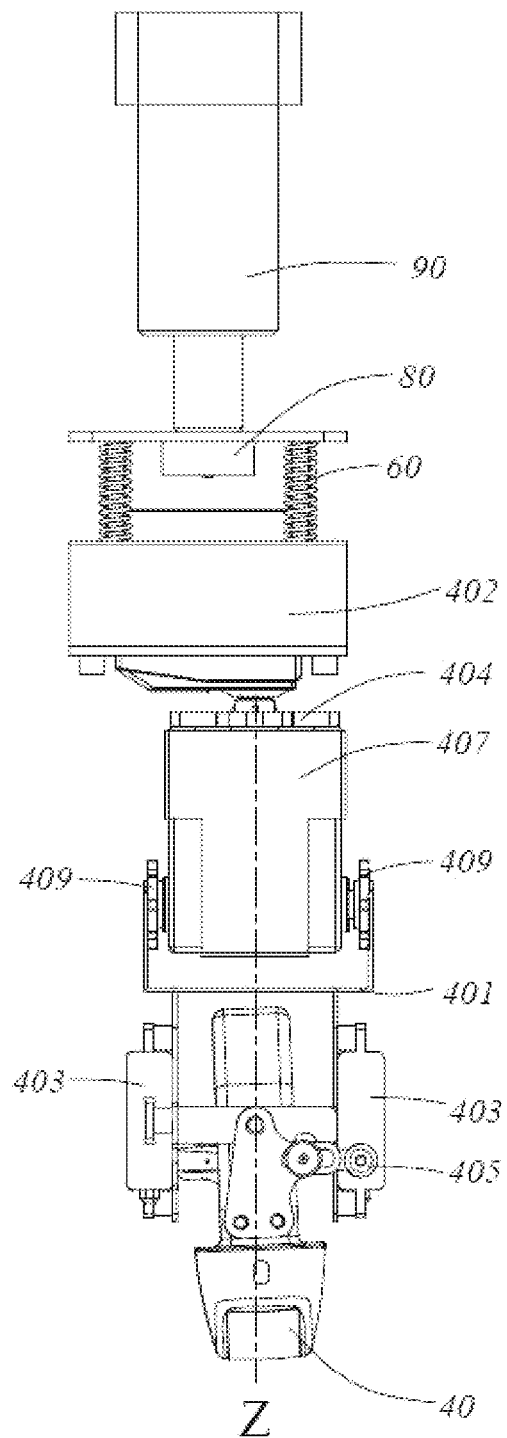
FIG. 6 is a schematic view of the probe of the probe robot device of FIG. 4 rotating around a first axis, wherein the probe is in a second position.
Figure 7:
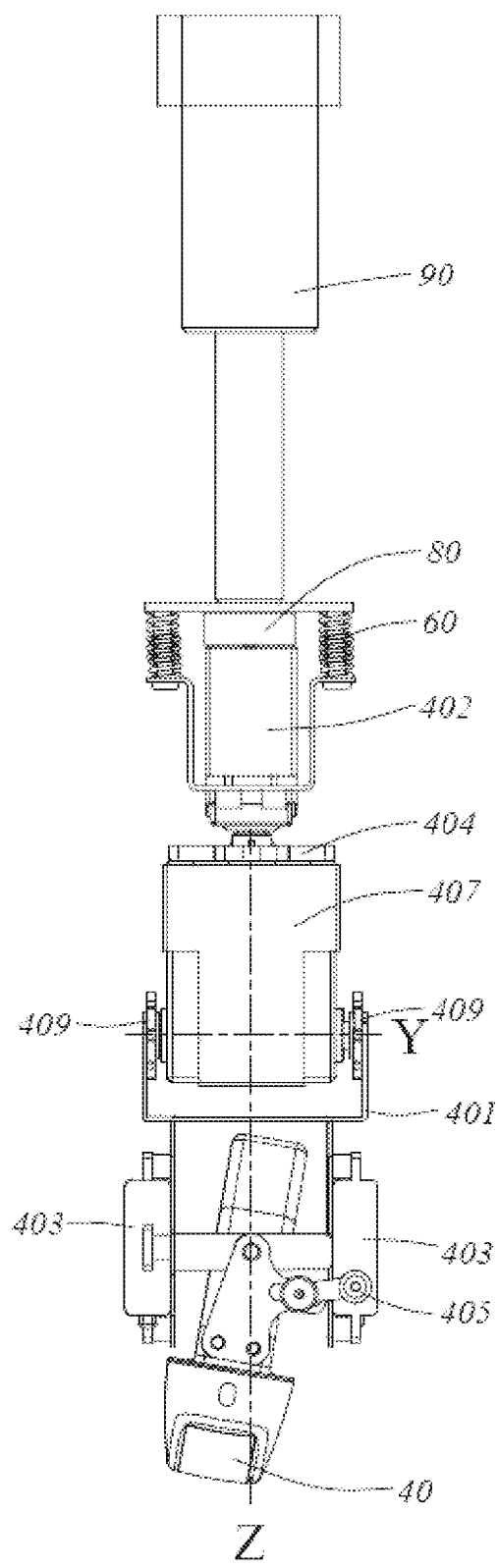
FIG. 7 is a schematic view of the probe in the probe robot device of FIG. 4 rotating around a second axis.
Figure 8:
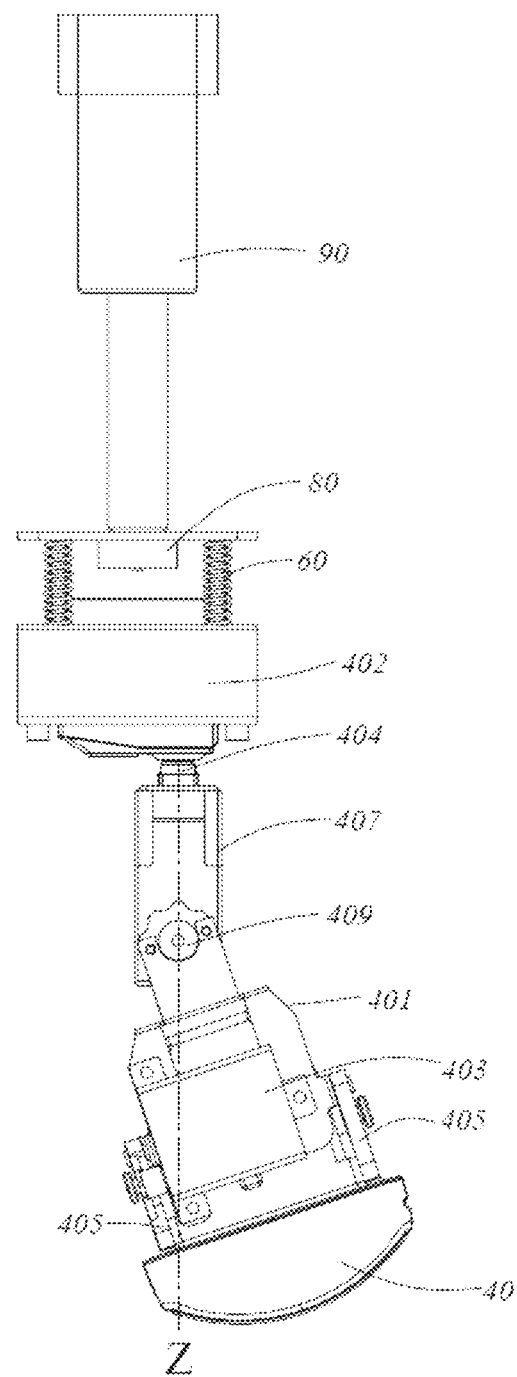
FIG. 8 is a schematic view of the probe of the probe robot device of FIG. 4 rotating around a third axis.
Figure 9:
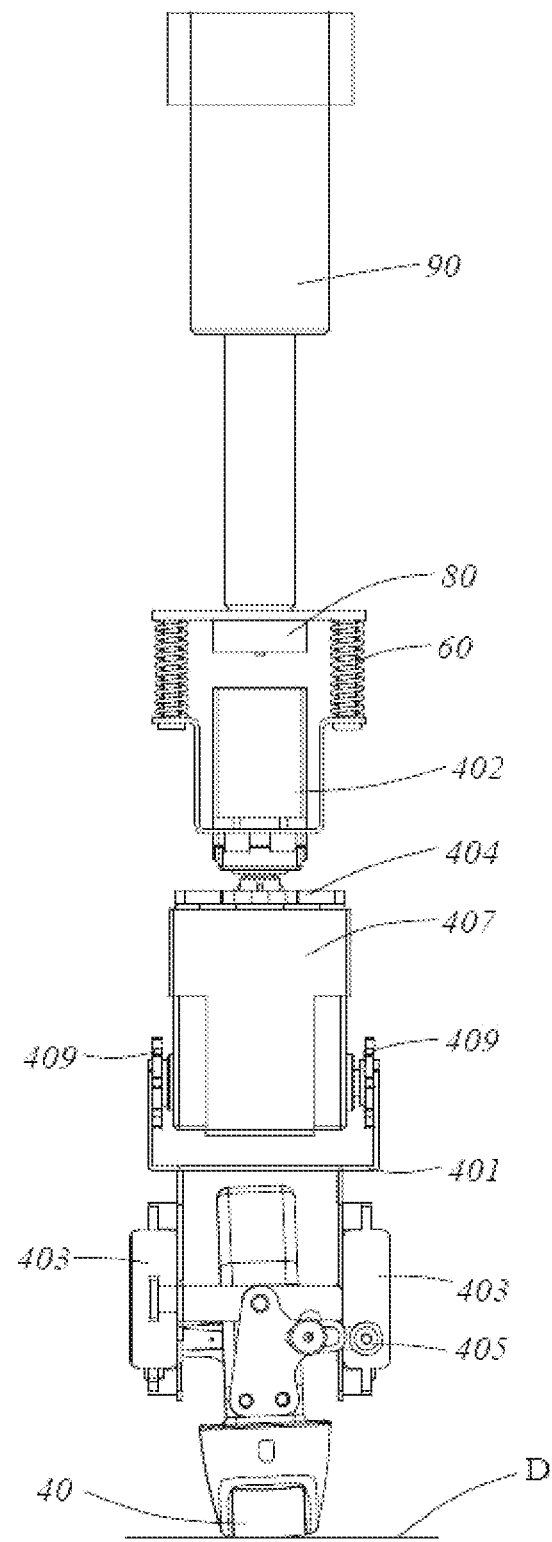
FIG. 9 is a movement schematic view of the probe robot device of FIG. 4, wherein the probe is just in contact with skin.
Figure 10:
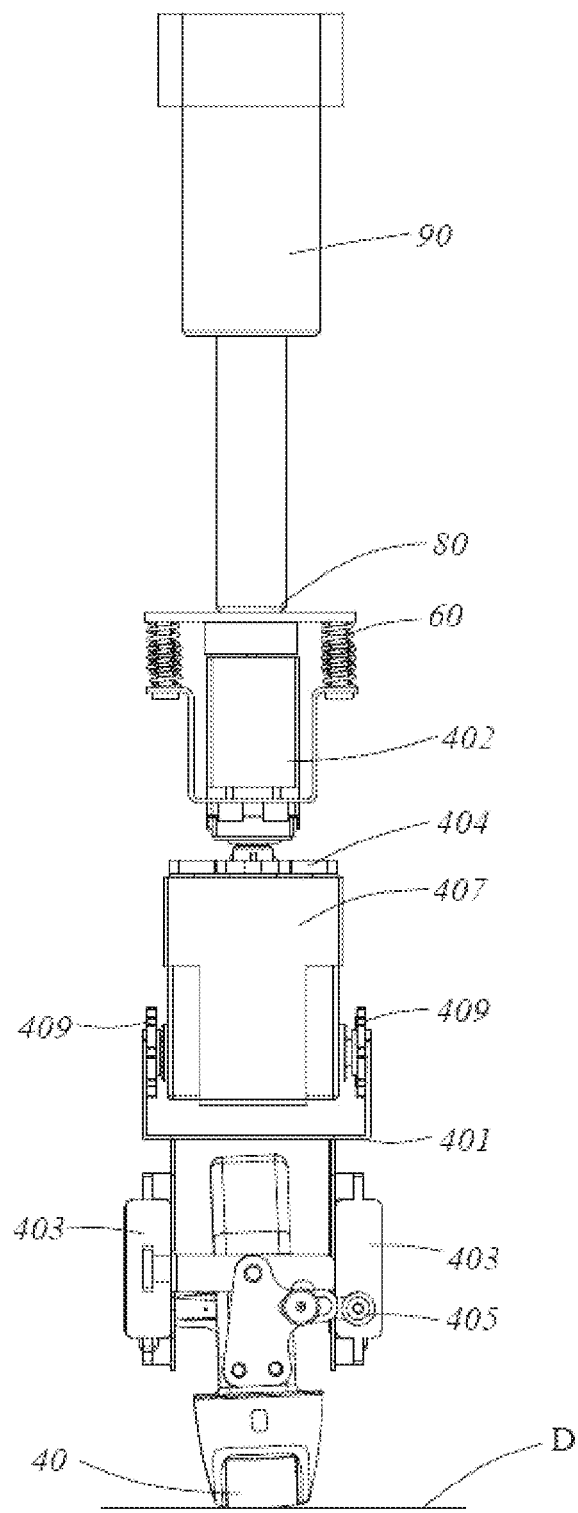
FIG. 10 is a movement schematic view of the probe robot device of FIG. 4, wherein the pressure of the probe against the skin exceeds a preset value.
Figure 11:
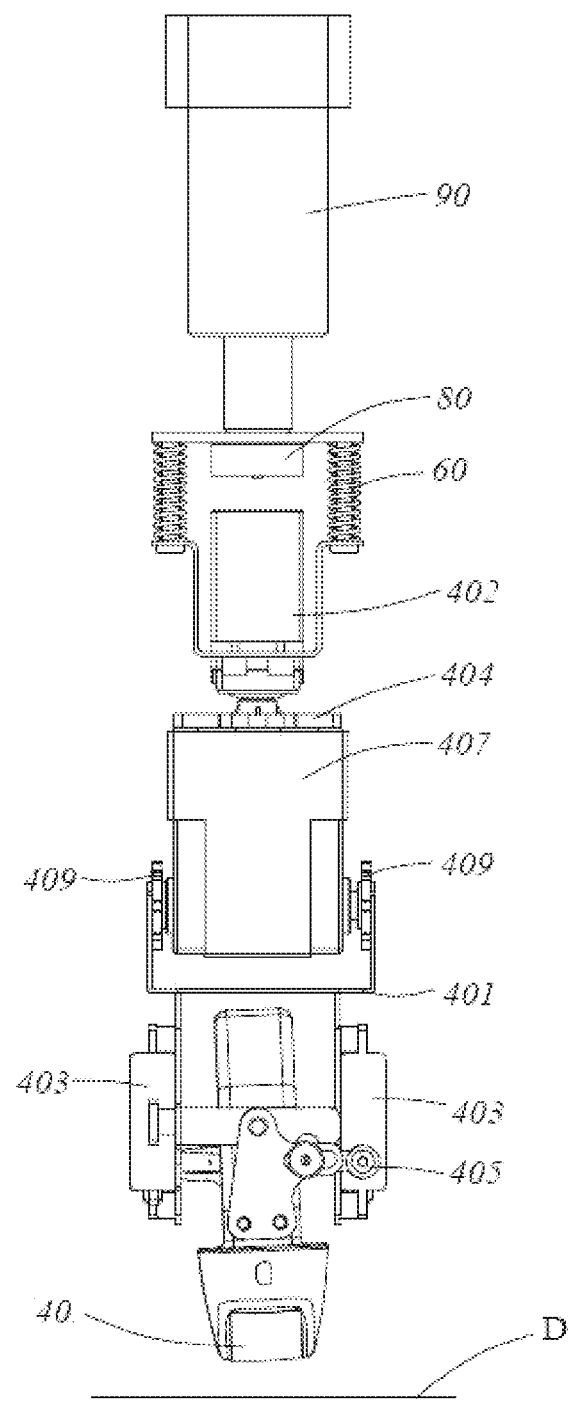
FIG. 11 is a movement schematic view of the probe robot device of FIG. 4, wherein an up and down movement structure drives the probe to move to ensure that the pressure of the probe against the skin is maintained within a preset range.

FIG. 1 to FIG. 3 show a preferred embodiment of the present invention. The preferred embodiment discloses a probe robot device 100, comprising a probe and a probe movement mechanism for controlling the movement of the probe. The probe is a device of ultrasonically transmitting and receiving a signal of ultrasonic type apparatus. The probe comprises a probe housing 20, a probe transducer 40 connected to the probe housing, and a probe connecting line (not shown) connected to the probe transducer 40. The probe transducer 40 is configured to collect a lesion. The probe connecting line is configured to transmit lesion information collected by the probe transducer 40. Therefore, the probe transducer 40 is a key component of the probe, and is responsible for electro-acoustic conversion as well as transmitting and receiving the ultrasonic waves. The probe connecting line is connected to the transducer 40 to send/receive an electrical signal to/from the transducer. A spring 60 is disposed between the probe housing 20 and the probe transducer 40. The probe transducer 40 can be telescopic vertically by means of the spring 60.

In the preferred embodiment, the probe movement mechanism is capable of controlling the probe transducer to perform rotational movement within a preset angle range. Preferably, the probe has the degrees of freedom of movement in three directions of the space, i.e., the probe transducer 40 can rotate around a X axis, a Y axis, and a Z axis in the drawings. FIG. 1 shows the degree of freedom of the probe in the first direction of the space, that is, the probe transducer can rotate around the Y axis. The angle of rotation is α. The Y axis is substantially parallel to the surface of the lesion, so that angle α is less than 180 degrees. Preferably, the angle α is less than or equal to 90 degrees, and such structure is relatively compact. FIG. 2 shows the degree of freedom of the probe in the second direction of the space, i.e. the probe transducer 40 can rotate around the Z axis. The Z axis is substantially perpendicular to the surface of the lesion, and the Z axis can be coincided with a central axis of the probe transducer 40. Therefore, the probe transducer 40 can rotate for 360 degrees around the Z axis. FIG. 3 shows the degree of freedom of the probe in the third direction of the space, the probe transducer 40 can rotate around the X axis, and the angle of rotation is β. The X axis is also substantially parallel to the surface of the lesion, so that the angle β is less than 180 degrees. Preferably, the angle β is less than or equal to 60 degrees, and such structure is relatively compact.

Referring to FIG. 4 to FIG. 8, the probe movement mechanism comprises a probe rotating structure, which mainly enables the probe transducer 40 to perform the rotational movement in a horizontal plane, that is, the probe transducer 40 can rotate around the Z axis. The probe rotating structure comprises a rotating steering engine 402 and a rotating steering engine connecting arm 404, wherein the rotating steering engine 402 drives the probe transducer 40 by the rotating steering engine connecting arm 404 to perform the rotational movement around the Z axis.

The probe movement mechanism further comprises a probe left and right swinging structure, which mainly enables the probe transducer to perform left and right swinging movement, that is, the probe transducer 40 can rotate around the X-axis within a preset angle range. The probe left and right swinging structure comprises a left and right swinging steering engine 403 and a left and right swinging steering engine connecting arm 405, wherein the left and right swinging steering engine 403 drives the probe transducer 40 by the left and right swinging steering engine connecting arm 405 to perform the rotational movement around the X axis, that is, the left and right swinging movement of the probe transducer 40.

The probe movement mechanism further comprises a probe front and back swinging structure, which mainly enables the probe transducer 40 to perform front and back swinging movement, that is, the probe transducer 40 can rotate around the Y axis within a preset angle range. The probe front and back swinging structure comprises a front and back swinging steering engine 407 and a front and back swinging steering engine connecting arm 409, wherein the front and back swinging steering engine 407 drives the probe transducer 40 by the front and back swinging steering engine connecting arm 409 to perform the rotational movement around the Y axis, that is, the front and back swinging movement of the probe transducer 40.

In a preferred embodiment, the probe transducer 40 is connected to the probe left and right swinging structure. The probe left and right swinging structure is mounted on a bracket 401. The bracket 401 is connected to the probe front and back swinging structure, wherein the probe front and back swinging structure drives the bracket and the probe left and right swinging structure to swing front and back together. The probe rotating structure is connected to the probe front and back swinging structure, wherein the probe rotating structure can control the probe front and back swinging structure and the probe left and right swinging structure to rotate around the Z axis together. It can be seen from the above that the degrees of freedom of the probe transducer 40 in three directions of the space can be controlled individually or in combination, thereby ensuring comprehensive detection during detection and correct detection results. In addition, every two axes of rotation are not absolutely perpendicular to each other, and may be at a preset angle as long as the requirement of scanning and examining the lesion by the probe transducer 40 can be met. Furthermore, whether the two axes of rotation are perpendicular or not, they may also be the axes intersecting or not intersecting in the space.

The above steering engines are a rotation control mechanism of the probe transducer 40, and have the characteristics of small size, large torque, simple external mechanical design, and high stability, etc. The steering engine mainly consists of a steering wheel, a reduction gear set, a position feedback potentiometer, a DC motor, a control circuit board, etc. The control circuit board receives the control signal from a signal line and controls the rotation of a motor. The motor drives a series of gear sets, and after speed reduction, the transmission is output to the steering wheel. An output shaft of the steering engine and the position feedback potentiometer are connected. While the steering wheel is rotating, the position feedback potentiometer is driven. The potentiometer will output a voltage signal to the control circuit board for feedback. Then the control circuit board determines the direction and speed of rotation of the motor according to the position, thereby achieving stop of the target. In the present embodiment, the steering engines are configured to control the rotation of the probe transducer, and the specific structure of the steering engines will not be repeated here.

According to the present embodiment, preferably, the probe robot device further comprises a probe pressure detecting structure, which mainly detects the pressure of the probe against the surface of the lesion. When the normal pressure is reached, a prompt sound or a vibration reminder will be provided, and when the normal pressure is exceeded, a prompt such as a warning will be provided, thereby ensuring the safety and comfort level of the scanning and examination of the probe transducer, and providing clear images. Specifically, the probe pressure detecting structure comprises a pressure sensor 80. The specific pressure sensor may be a strain sensor, a piezoelectric sensor, a piezoresistive sensor, etc. The pressure of the probe against the surface of the lesion can be controlled by the probe pressure sensor, so as to prevent the influence on the detection results caused by a too small pressure or the discomfort of the patient caused by a too large pressure.

According to the present embodiment, further preferably, the probe robot device further comprises an up and down movement mechanism 90, by which the movement of the probe in a direction perpendicular to the surface of the lesion is controlled. That is to say, the probe robot device can be mounted on a robotic arm for use. By means of the robotic arm, the probe transducer is controlled to move in a direction close to or away from a detected surface and/or move on the detected surface. In this way, no manual operation is required, and the pressure detecting structure will give a signal to automatically raise the pressure to the pressure range for use when the pressure range is exceeded.

It can be known from the above embodiment that the probe movement mechanism and the probe in the probe robot device according to the present invention can be constructed as an integral unit, that is, the probe movement mechanism can be disposed inside the probe housing. Of course, a more preferred manner is that the probe movement mechanism is detachably connected to the probe housing and drives the probe transducer to perform rotational movement by driving the probe housing. In this way, the probe is replaceable since it has many different models. The probe robot device is allowed to realize different functions by changing the probe.

The specific operation of the probe robot device in the above embodiment is as follows. The probe robot device is enabled to touch skin D and is continuously pressed down. The spring 60 is compressed, the pressure sensor 80 is touched, and when a certain pressure is reached, the up and down movement mechanism 90 will functioned. The up and down movement mechanism 90 of the probe robot device controls the probe to move upwards, and the pressures of the probe and the skin can be guaranteed to be within a certain range by program control.

As long as the doctor puts the probe in a physical examination area of the patient, the probe will automatically perform up, down, left, and right rotational movement according to a program, and automatically retrieve and store the pictures of the lesion. No professional scanning and examination technology for the doctor is required. Anyone can use the probe robot device as long as the probe is placed in the place to be scanned and examined, the probe will automatically scan and examine, and retrieve and save the pictures. The stored pictures can be used for solving the problem of diagnosis by cloud diagnosis. In this way, the probe can enter the household and the patient can see the doctor at home by himself. Or a simple robotic arm instead of human hands can be used to hold the probe, so that the operation of people is not required.

The probe transducer of the probe robot device according to the present invention can perform the rotation and positioning movements of multiple directions, so that the information of the scanned and examined lesion is more comprehensive, and the operation is simpler and more convenient. The examination comfort level of the patient and clearer images obtained by scanning and examining can be ensured by the pressure sensor. Moreover, the probe robot device according to the present invention has lower requirements on a doctor and can greatly reduce the workload of the doctor. In addition, the sales group of the probe in the probe robot device according to the present invention is no longer a medical institution, and can enter thousands of households. Thus, the probe robot device can be used by everyone.

It should be understood that although the specification is described according to the embodiments, it is not necessary for each embodiment to contain an independent technical solution, and the description of the specification is merely for the sake of clarity. Those skilled in the art should take the specification as a whole, the technical solutions in the embodiments may also be combined appropriately to form other embodiments appreciable by those skilled in the art.

The series of foregoing detailed description of the preferred embodiments is merely specific explanation of feasible embodiments of the present invention, but not limiting the protective scope of the present invention. The equivalent embodiments or changes made without departing from the spirit of the present invention should be within the protection scope of the present invention.

What is claimed is:

1. An ultrasonic probe head, comprising: a probe housing; a probe transducer connected to the probe housing, and a probe connecting line connected to the probe transducer to transmit information collected by the probe transducer, wherein the probe robot device further comprises a probe movement engine assembly, the probe movement engine assembly is disposed inside the probe housing, the probe movement engine assembly is configured to control the probe transducer to respectively perform rotational movement relative to the probe housing around at least two angled axes within a predefined angle, wherein the probe movement engine assembly comprises a probe swinging engine, the probe swinging engine comprises probe front and back swinging engine for controlling swinging type rotational movement of the probe transducer in front and back directions, and probe left and right swinging engine for controlling swinging type rotational movement of the probe transducer in left and right directions, wherein the ultrasonic probe head further comprises a bracket for mounting the probe left and right swinging engine, wherein the bracket is connected to the probe front and back swinging engine, and the probe front and back swinging engine is configured to drive the bracket and the probe left and right swinging engine to perform front and back swinging type rotational movement together.

2. The ultrasonic probe head according to claim 1, wherein the probe movement engine assembly comprises a probe rotating engine, wherein the probe rotating engine is configured to control the probe transducer to rotate around a vertical axis perpendicular to the surface of a lesion.

3. The ultrasonic probe head according to claim 2, wherein the probe swinging engine is configured to control the probe transducer to perform rotational movement around an axis parallel to a plane of the lesion within a range less than 180 degrees, the probe swinging engine is connected to the probe rotating engine, and the probe rotating engine is configured to control the probe swinging engine and the probe transducer to rotate together around a vertical axis perpendicular to the surface of the lesion.

4. The ultrasonic probe head according to claim 2, wherein the probe rotating engine comprises a steering engine and a steering engine connecting arm connected between the steering engine and the probe transducer, the steering engine controls the rotational movement of the probe transducer by the steering engine connecting arm.

5. The ultrasonic probe head according to claim 1, wherein the probe swinging engine comprises a steering engine and a steering engine connecting arm connected between the steering engine and the probe transducer, wherein the steering engine controls the rotational movement of the probe transducer by the steering engine connecting arm.

6. The ultrasonic probe head according to claim 1, wherein the probe robot device further comprises a probe pressure sensor, the probe pressure sensor is configured to detect a pressure of the probe against a detected surface.

7. The ultrasonic probe head according to claim 6, wherein the probe robot device further comprises an up and down movement engine for controlling the probe transducer to move in a direction close to or away from the detected surface, wherein when the pressure is outside a predefined range, the up and down movement engine will control the movement of the probe transducer according to a signal given by the pressure sensor, such that the pressure is within the predefined range.

8. The ultrasonic probe head according to claim 6, wherein the probe robot device is further configured to prompt when the pressure reaches a predefined value.

9. The ultrasonic probe head according to claim 1, wherein a spring is disposed between the probe housing and the probe transducer, the probe transducer can be telescopic vertically by means of the spring.

10. The ultrasonic probe head according to claim 1, wherein the probe movement engine assembly comprises three steering engines, the three steering engines are configured to control the rotation of the probe transducer in three directions of the space.

11. The ultrasonic probe head according to claim 6, when the pressure detected by the pressure sensor reaches a predefined value, the probe head is configured to provide a prompt sound or a vibration reminder; when the pressure detected by the pressure sensor exceeds the predefined value, the probe head is configured to provide a warning.

* * * * *